United States Patent
Greter et al.

(10) Patent No.: US 9,061,257 B2
(45) Date of Patent: Jun. 23, 2015

(54) APPARATUS FOR MIXING AND DISCHARGING A FLUID PRODUCT AND RELATED SYSTEM

(75) Inventors: Andy Greter, Baar (CH); Rochus Stockli, Buochs (CH); Samuel Kaufmann, Muri (CH); Wilhelm A. Keller, Merlischachen (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 888 days.

(21) Appl. No.: 13/260,627

(22) PCT Filed: Apr. 8, 2010

(86) PCT No.: PCT/CH2010/000091
§ 371 (c)(1), (2), (4) Date: Sep. 27, 2011

(87) PCT Pub. No.: WO2010/124401
PCT Pub. Date: Nov. 4, 2010

(65) Prior Publication Data
US 2012/0026823 A1 Feb. 2, 2012

(30) Foreign Application Priority Data
Apr. 28, 2009 (CH) .................................... 0660/09

(51) Int. Cl.
| | |
|---|---|
| *B01F 5/06* | (2006.01) |
| *B01F 3/10* | (2006.01) |
| *B01F 11/00* | (2006.01) |
| *B01F 13/00* | (2006.01) |
| *A61B 17/88* | (2006.01) |
| *B01F 15/00* | (2006.01) |

(52) U.S. Cl.
CPC ............... *B01F 3/10* (2013.01); *A61B 17/8825* (2013.01); *B01F 5/0685* (2013.01); *B01F 11/0082* (2013.01); *B01F 13/002* (2013.01); *B01F 13/0023* (2013.01); *B01F 15/00506* (2013.01);
(Continued)

(58) Field of Classification Search
CPC ..................................................... B01F 13/0023
USPC ........................ 366/176.3, 130, 189; 604/416
See application file for complete search history.

(56) References Cited

U.S. PATENT DOCUMENTS 3,756,390 A * 9/1973 Abbey et al. .................. 206/219
4,776,704 A * 10/1988 Kopunek et al. .............. 366/184
(Continued)

FOREIGN PATENT DOCUMENTS

| DE | 102 42 984 A1 | 3/2004 |
|---|---|---|
| DE | 10 2005 030 510 A1 | 1/2007 |

(Continued)

*Primary Examiner* — Charles Cooley
*Assistant Examiner* — Marc C Howell
(74) *Attorney, Agent, or Firm* — Sughrue Mion, PLLC

(57) ABSTRACT

A discharge apparatus for discharging a fluid product comprises a housing (1) having an outlet (6) at a front housing end, a discharge member (3) which is mounted movably in the housing and the rear end of which protrudes from the rear housing end, and a mixing device (2) for mixing the fluid product inside the housing. The fluid product is provided in a housing volume (25) formed between the outlet and the discharge member. The fluid product is discharged through the outlet out of the housing by advancing the discharge member inside the housing from a rear position into a front position in the direction of the outlet. The mixing device comprises a mixing tube (11), which is mounted movably between the housing and the discharge member in the housing, and at least one mixing element (12), which is provided at the front end of the mixing tube and disposed inside the housing volume.

16 Claims, 8 Drawing Sheets

(52) U.S. Cl.
CPC . *B01F 2215/0029* (2013.01); *B01F 2215/0034* (2013.01)

(56) References Cited

U.S. PATENT DOCUMENTS

| | | | |
|---|---|---|---|
| 5,372,586 A * | 12/1994 | Haber et al. | 604/89 |
| 6,406,175 B1 | 6/2002 | Marino | |
| 8,356,927 B1 * | 1/2013 | Lordi et al. | 366/130 |

| | | | |
|---|---|---|---|
| 2002/0049405 A1 | 4/2002 | Deslauriers et al. | |
| 2004/0122359 A1 * | 6/2004 | Wenz et al. | 604/82 |
| 2007/0217282 A1 | 9/2007 | Lidgren et al. | |

FOREIGN PATENT DOCUMENTS

| | | |
|---|---|---|
| DE | 20 2007 007 796 U1 | 9/2007 |
| EP | 1 920 738 A2 | 5/2008 |
| GB | 2 338 428 A | 12/1999 |
| WO | WO 8400011 * | 1/1984 |

* cited by examiner

APPARATUS FOR MIXING AND DISCHARGING A FLUID PRODUCT AND RELATED SYSTEM

CROSS REFERENCE TO RELATED APPLICATIONS

This application is a National Stage of International Application No. PCT/CH2010/000091 filed Apr. 8, 2010, claiming priority based on Switzerland Patent Application No. 00660-09 filed Apr. 28, 2009, the contents of all of which are incorporated herein by reference in their entirety.

TECHNICAL FIELD

The present invention relates to a discharge apparatus for discharging a fluid product, with a mixing device for mixing the fluid product in the discharge apparatus.

PRIOR ART

Discharge apparatuses for discharging a fluid product, such as those to which the present invention refers, are used in many different applications, for example in medical technology. Such a discharge apparatus may, for example, be in the form of a single-cylinder syringe which comprises a cylindrical housing, with an outlet on the front housing end, and a piston or plunger which is received in the housing and projects out of the housing at the opposite rear end of the latter. The fluid product is arranged inside the housing between the housing outlet and the piston. By the piston being advanced within the housing from a rear position in the direction of the outlet to a front position, the fluid product is discharged out of the housing through the outlet.

Some fluid products which are to be applied by means of such a discharge apparatus have to be stirred up or intermixed immediately before use. The fluid product may in this case be stored, already fully composed, in the discharge apparatus, or it is possible that a plurality of components of the fluid product have to be combined and intermixed inside the discharge apparatus. In the case of fluids of very high viscosity, for example, it is not sufficient to mix by shaking the discharge apparatus. To enable sufficient mixing to be carried out within the discharge apparatus, there are discharge apparatuses which comprise a mixing device.

For the production and use of bone cement, a mixing and injection appliance is known, for example from U.S. Pat. No. 6,406,175 B1. The appliance comprises a housing cylinder which is closed at both ends by a cover. A rod is led through the covers and can be displaced in the longitudinal direction inside the housing by means of a handle. A mixing disk is firmly attached to the rod inside the housing, so that, as a result of the longitudinal movement, the mixing disk can be displaced inside the housing in order to mix a mixing product. A piston element is attached to one cover inside the housing. After mixing has ended, the mixing disk is pushed into a front position, and that part of the rod which projects out of the housing at the opposite end is broken off. The mixing disk is subsequently drawn into a rear position in which it butts against the piston element. By the mixing disk being rotated by means of the rod, the piston element is fastened to the mixing disk. As soon as the piston element is fastened to the rod, said piston element can be released from the inside of the housing cover, and the mixing product can be discharged through the orifice which occurred at the opposite housing end when the rod was broken off.

An appliance for administering a curing compound is known from EP 1 920 738 A2. The appliance has essentially the set-up of a conventional syringe with a syringe housing including an outlet, and with an expulsion member mounted therein. Inside the syringe is provided a mixing space in which the mixing product can be mixed by means of a mixing element which is arranged on the expulsion member. A piston part is mounted on the syringe housing at the end located opposite the outlet and is fixed in relation to the housing during the mixing operation. At the end of the mixing operation, the expulsion member together with the mixing element is drawn toward the piston part which, by the expulsion member being rotated, is released from the housing and is fastened to the expulsion member. By the expulsion member being advanced by means of the piston part, the mixture can be expelled through the outlet.

In the known discharge and mixing apparatuses, it is difficult to mix and discharge only small quantities of a fluid product. In apparatuses with a large housing cross section, the stroke travel for carrying out mixing by means of a mixing rod is often very short, so that sufficient mixing of the fluid cannot be ensured. In appliances with small diameter and with a long length of the mixing chamber, the mixing rod has to be made very thin, and therefore it may become unstable during a mixing operation.

An object of the present invention is to provide a discharge apparatus having a mixing device, which enables satisfactory mixing of a fluid product in the apparatus, is of stable construction and allows simple handling.

SUMMARY OF THE INVENTION

According to the present invention, a discharge apparatus for discharging a fluid product, such as, for example, a liquid or pasty product, is provided, which comprises a housing with an outlet at a front housing end, a discharge member which is mounted moveably in the housing and projects with its rear end out of a rear housing end, and a mixing device for mixing the fluid product inside the housing. A housing volume, in which the fluid product is provided, is formed inside the housing between the outlet on the front end of the housing and the discharge member. As a result of the discharge member being advanced, inside the housing from a rear position into a front position toward the housing outlet, the fluid product is discharged out of the housing through the outlet. According to the invention, the mixing device has a mixing tube, which is mounted moveably in the housing between the housing and the discharge member, and at least one mixing element, which is provided at the front end of the mixing tube and is arranged inside the housing volume.

The housing is preferably of cylindrical design and may, for example, be in the form of a syringe housing. The outlet on the front end of the housing may be formed by an outlet nozzle of small diameter which is integrated in the housing. It is also possible for the outlet to be designed as a simple housing orifice. Above the outlet, for example, further accessories may be arranged, which are especially suitable for discharging specific fluids or for specific applications. During a mixing operation by means of the discharge apparatus, the housing outlet is closed by a removable cover.

The discharge member is introduced into the housing at the rear housing end. The discharge member is preferably formed by an elongate cylinder, of which the front end, which comes to lie inside the housing, is closed by a front face. The front face forms a discharge face or a piston for discharging the fluid product out of the housing. The housing volume for receiving the fluid product is formed between the front housing termination, in which the outlet is located, the inner circumferential wall of the housing and the discharge face for the discharge member. By the discharge member being advanced from a rear position to a front position in the direction of the outlet, this housing volume is reduced and the fluid is displaced through the outlet. According to the invention, the discharge member may be arranged at least partially within the mixing device. Furthermore, the mixing device may be displaced in accompaniment when the discharge member is being advanced for the purpose of discharging the product.

According to the invention, the mixing tube is mounted between the housing and the discharge member. The discharge member is preferably mounted moveably within the mixing tube. In this case, preferably, the outer wall of the mixing tube is adjacent to the inner wall of the housing and the outer wall of a tubular discharge member or of another piston element is adjacent to the inner wall of the mixing tube. The cylindrical housing, the mixing tube and the discharge member can be displaced telescopically in relation to one another in the longitudinal direction. The mixing tube projects with its rear end out of the rear housing end. The discharge member, in turn, projects with its rear end out of the rear end of the mixing tube. The rear end of the mixing tube which projects out of the housing may have a grip block, on which the mixing tube can be gripped and moved in relation to the housing and discharge member. The housing may have a housing abutment at the rear end and the discharge member may have a stop abutment at the rear end, between which abutments the grip block can be displaced to and fro. The housing abutment and the stop abutment thus limit the displacement movement of the mixing tube.

The mixing tube according to the present invention projects with its front end into the housing volume in which the fluid product is located. The at least one mixing element is arranged at this end of the mixing tube. The at least one mixing element may in this case project beyond the end of the mixing tube, but preferably comes to lie within the front orifice at the margin of the mixing tube. The at least one mixing element may be formed in one piece with the mixing tube. Suitable mixing elements are, for example, individual blades or strips which, for example, are arranged in a cruciform or star-shaped manner at the front end of the mixing tube in such a way that a passage into the interior of the mixing tube remains. Preferably, mixing blades are arranged obliquely with respect to the longitudinal axis of the mixing tube, so that a better mixing behavior can be brought about.

The mixing tube is inserted with its outer circumference having an exact fit in the inner circumference of the housing in such a way that movement between the housing and mixing tube remains possible. The transition between the mixing tube outer wall and the housing inner wall is made fluid-tight. For this purpose, for example, an O-ring, which is adjacent to the outer circumference of the mixing tube, may be provided on the inner circumference of the housing. It is also possible to attach to the outer circumference of the mixing tube a sealing lip which bears in the circumferential direction against the inner circumference of the housing. It is necessary to ensure that the seal allows sufficiently simple displacement of the mixing tube in the housing. The transition between the outer circumference of the discharge member to the inner circumference of the mixing tube is likewise made fluid-tight. The discharge member is preferably of tube-like design, so that the outer circumference of the discharge tube comes to lie against the inner circumference of the mixing tube. Once again an O-ring or a sealing lip or another seal may be provided between the discharge tube and mixing tube.

To mix the fluid product in the housing volume, the discharge member is brought into a rear position and is held at rest in relation to the housing. The mixing tube is then moved to and fro in relation to the housing and to the discharge member, so that the mixing elements are led through the housing volume, the fluid product being fully mixed. The spacing of the housing abutment and of the stop abutment on the discharge member, between which the mixing tube is moved to and fro, may advantageously be dimensioned in such a way that, in a front position, the front edge of the at least one mixing element abuts against the bottom face of the housing and, in a rear position, the rear edge of the at least one mixing element abuts against the piston face of the discharge member. Preferably, the mixing tube is mounted rotatably in relation to the housing and/or to the discharge member. As a result, the mixing elements can be guided over the bottom face of the housing and the discharge face of the discharge member and thus remove residual constituents of the fluid product from these faces.

When the mixing tube is being moved forward and backward inside the housing volume, the fluid product is led through between the mixing elements into the interior of the mixing tube during movement in the direction of the housing outlet. During movement in the direction of the discharge member, the fluid product is expelled from the discharge face of the discharge member past the mixing elements out of the mixing tube into the housing volume.

In a discharge apparatus according to the present invention, it is possible to fully mix even small volumes of a fluid product reliably, since the mixing tube is made stable by virtue of the tubular construction and the inner circumferential wall of the housing can form a guide for the mixing tube. The mixing tube can therefore be moved vigorously inside the housing in order to generate pronounced turbulence of the fluid product in the housing, without warping or bending occurring.

In a preferred embodiment of the discharge apparatus according to the present invention, a detaining device for the releasable detention of the discharge member in a rear position is provided on the housing. The detaining device ensures that, during the mixing operation, the discharge member is fixed in relation to the housing and is not moved together with the movement of the mixing tube. After the mixing operation has ended, the detention of the discharge member can be released and the discharge member can be advanced in relation to the housing for the purpose of discharging the fluid product.

In a first variant of a detaining device, at least one sliding arm is provided on the discharge member and at least one sliding channel, into which the sliding arm can be introduced slideably, is provided on the housing. Preferably, two sliding arms are arranged in parallel next to the discharge member. For example, the sliding arms may project from a common end plate which is arranged at the rear end of the discharge member. Moreover, the end plate may serve as a stop abutment for the grip block of the mixing tube. A sliding channel is provided on the housing for each of the two sliding arms. The sliding channels may, for example, be shaped out from the housing material next to the cylindrical part of the housing. The sliding channel may also be fastened as a separate element to the housing. In the assembled state of the discharge member and of the housing, the preferably tubular discharge member projects into the cylindrically designed housing, while the sliding arms running parallel thereto project into the sliding channels. The sliding arms in the sliding channels thus form a guide for the discharge member during movement forward and backward inside the housing, independently of a detaining function.

To detain the discharge member on the housing, the sliding arms may have provided on them latching means which cooperate with couterlatching means on or in the sliding channel and allow releasable latching. The latching means may be formed, for example, by at least one latching arm projecting flexibly from the sliding arm. The couterlatching means may be formed by at least one latching orifice in the sliding face of the sliding channel. The latching arms and latching orifices are positioned in such a way that the latching arms engage into the latching orifices when the discharge member is in a rear position in relation to the housing.

In another variant, the detaining device is formed by at least one latching wing on one of the housing and discharge member and by at least one latching groove on the other of the housing and discharge member. Preferably, two latching wings are provided on the housing and two latching grooves are provided in the discharge member. The latching wings project radially opposite one another from the outer circumference of the housing. The latching grooves are arranged on outriggers offset laterally and parallel to the discharge member. When the discharge member is rotated in relation to the housing, the latching wings come to lie within the latching grooves. A further rotation is made impossible in that the latching wings abut abutments within the latching grooves. Detention is released by rotation in reverse. As soon as the latching wings engage into the latching grooves, longitudinal movement of the discharging member in relation to the housing is no longer possible. Preferably, the grip block of the mixing tube comes to lie between the parallel-running outriggers of the discharge member. Especially preferably the outer face of the grip block slides along the inner face of the outriggers.

In a further embodiment of a discharge apparatus according to the present invention, a blocking device for blocking movement of the discharge member in relation to the housing in the rear position of the discharge member opposite to the direction of advance is provided. The blocking device prevents the discharge member from being inadvertently drawn out of the housing completely. The mixing tube is preferably designed with a rear abutment, such as, for example, the grip block, which, in the event of movement opposite to the direction of advance in relation to the discharge member, abuts against a stop abutment at the rear end of the discharge member, so that this movement is blocked. On account of the blocking device for movement opposite to the direction of advance for the discharge member in the rear position of the latter, the stop abutment also prevents the mixing tube from being drawn out of the housing completely.

The blocking device may be formed, for example, on at least one sliding arm with latching arm and at least one sliding channel with latching orifice, as described above. To block the discharge member, a latching arm latched into the latching orifice abuts with its end against a margin of the latching orifice, so that the latching orifice forms an abutment for the latching arm end.

Movement of the discharge member in relation to the housing is possible in the direction of advance, in that the flexibly designed latching arm slides along at the margin of the latching orifice and is thereby bent flexibly radially inward. That face of the latching arm which slides along at the margin of the latching orifice of the housing may have a latching boss which offers resistance to the advancing movement of the discharge member. The latching boss makes it possible to detain the discharge member in the rear position in relation to the housing. In order to move the discharge member in the direction of advance, there must first be increased effort to overcome resistance of the latching boss. As soon as the resistance has been overcome, the latching arm is bent flexibly inward and the discharge member can be moved in the direction of advance. By the butting of the mixing tube at the rear against the stop abutment of the discharge member, during an advancing movement of the discharge member the mixing tube is moved jointly with the discharge member and is pushed into the housing.

Furthermore, in a discharge apparatus according to the present invention, a guide device for guiding the mixing tube during displacement along the discharge member may be provided. A guide device may be formed, for example, by at least one sliding arm on the discharge member, said sliding arm running parallel to the latter, and by at least one sliding leadthrough on a grip block of the mixing tube. The sliding arm of the discharge member is received slidably in the sliding leadthrough. The sliding arm on the discharge member serves for stabilizing the mixing tube during its movement in relation to the discharge member and to the housing. As already described above, the sliding arm of the discharge member may issue into a sliding channel on the housing, with the result that the sliding arm is also stabilized.

In order to allow a rotational movement of the mixing tube about the discharge member, the sliding leadthrough on the grip block may be of slot-like design in the form of a segment of a circle, so that the sliding arm can be rotated within the slot from one end to the other end. The segment of a circle of the sliding leadthrough in the grip block therefore defines the possible angle of rotation of the mixing tube about the discharge member.

In another discharge apparatus according to the present invention, the discharge member may have at the rear end an end plate, from which are provided outriggers or webs running parallel to the discharge member on both sides of the latter. The outriggers thus enclose between them the discharge tube of the discharge member. Latching grooves are located at the front end of the outriggers. Two latching wings projecting on opposite sides are provided at the rear end of the housing. When the discharge member is pushed forward and backward into the housing, the latching wings come to lie between the outriggers on the discharge member. In the rear position of the discharge member, the outriggers end behind the latching wings of the housing, so that the housing can be rotated in relation to the webs. However, the latching grooves project from the front face of the outriggers in such a way that the latching wings latch into these latching grooves when the housing is rotated. The latching wings are then held in the axial direction by the latching grooves, so that the discharge member cannot be moved in the longitudinal direction in relation to the housing.

The outriggers of the discharge member with the latching grooves and the latching wings on the housing thus form with one another a detaining device for the releasable detention of the discharge member in the rear position on the housing.

The grip block at the rear end of the mixing tube of a mixing device of the discharge apparatus can come to lie between the webs of the discharge member and preferably bears with its sides against the insides of the outriggers. The insides of the outriggers thus form a guide face for the grip block of the mixing tube. By the grip block being gripped, the mixing tube can be moved to and fro in the longitudinal direction of the discharge member between the closing plate of the discharge member and the latching wings. In this case, the closing plate of the discharge member and the latching wings of the housing serve as abutments for the movement of the mixing tube.

After the end of the mixing operation, the housing can be rotated out of the latching grooves again until the latching wings come to lie in the interspace of the outriggers. In this position, the discharge member can be advanced in relation to the housing and the mixture can be discharged.

A discharge apparatus according to the present invention may already be filled with a fluid product which, however, should be fully mixed thoroughly before application by the discharge apparatus. It is also possible, however, to fill a discharge apparatus according to the present invention with a fluid product only prior to use. In this case, it is also possible to fill the discharge apparatus with a plurality of different components. It is basically also possible that one of the components is already provided in the discharge apparatus, such as, for example, a powder component, and the discharge apparatus is filled with a further component only shortly before use, in order to be mixed with the component already located in the discharge apparatus. To fill the discharge apparatus, it is possible to connect to the outlet of the housing, for example, a syringe, by means of which a product or component can be injected into the housing. Alternatively, it is also possible to connect the outlet of the housing to a fluid reservoir and to suck the fluid into the housing by means of the discharge apparatus. For this purpose, the discharge member is drawn, together with the mixing tube, from a front position into a rear position in relation to the housing, so that a suction action occurs at the outlet of the housing and the fluid is sucked into the discharge apparatus.

According to the invention, therefore, a system composed of a discharge apparatus and of a loading apparatus, by means of which the discharge apparatus can be loaded, is provided. Preferably, one component of a fluid mixture is already located in the housing volume of the discharge apparatus, and a second component of the fluid mixture is introduced into the discharge apparatus by means of the loading apparatus. With the aid of the mixing device of the discharge apparatus, the first and the second components can be mixed inside the discharge apparatus.

A discharge apparatus according to the present invention allows uncomplicated use even of small fluid quantities and reliable intermixing of a fluid product inside the discharge apparatus. Bending or warping of the mixing device within the housing of the discharge arrangement, with the result that the functionality of the discharge apparatus is adversely impaired, is not possible, since the mixing device is provided within the discharge apparatus in a stable manner and is simple to actuate.

BRIEF DESCRIPTION OF THE DRAWINGS

Preferred embodiments of the invention are illustrated below by means of the drawings which serve merely for explanatory purposes and are not to be interpreted restrictively. Features of the invention which are disclosed in the drawings are to be considered individually and in any combination as belonging to the disclosure of the invention. In the drawings.

FIG. 1 shows an exploded illustration of the individual structural parts of a first embodiment of a discharge apparatus according to the present invention. The discharge apparatus comprises a housing 1, a mixing device 2, a discharge member 3 and a cover cap 4. The housing 1 has an elongate housing cylinder 5 with an outlet 6 at the front end and with laterally projecting holding wings 7 at the rear end. Two strips 8 extend parallel to the housing cylinder 5 on opposite sides and are fastened at least to the front and the rear end of the housing cylinder 5. Within each of the strips 8 is arranged a sliding channel which is open at the rear end of this strip and extends as far as the front end. The outlet 6 is surrounded by a sleeve 9 which has a thread on its inner circumference and which serves as a fastening means for accessories which are to be connected to the discharge apparatus. Other fastening devices are basically also possible, such as, for example, plug or clamping connections. Along the longitudinal side of the strips 8, the sliding channels have latching orifices 10 which are located at a rear region of the strips.

Figure 1:
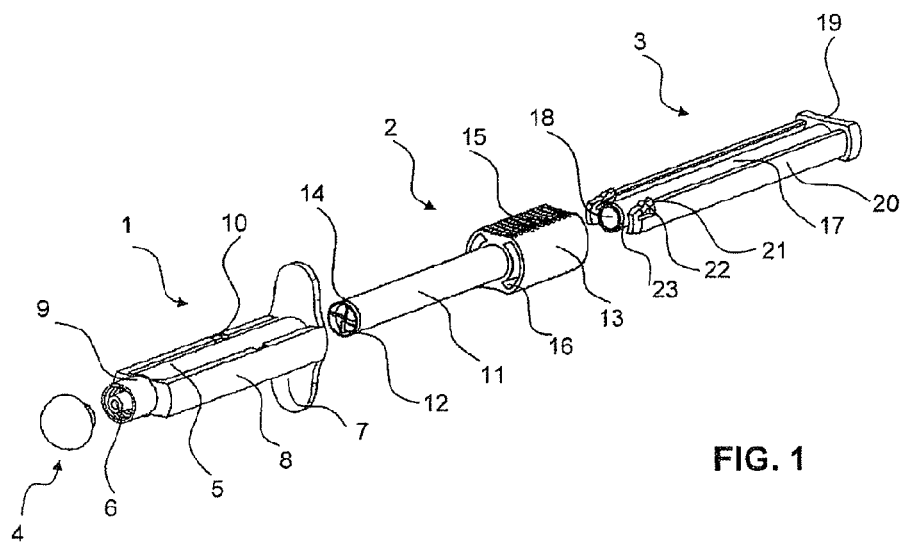
FIG. 1: shows an exploded illustration of a first embodiment of a discharge apparatus according to the present invention.

The mixing device 2 comprises an elongate mixing tube 11, at the front end of which mixing elements 12 are arranged and at the rear end of which a grip block 13 is arranged. The outer circumference of the mixing tube 11 is coordinated with the inner circumference of the housing cylinder 5 in such a way that the mixing tube bears against the housing cylinder, but is displaceable and rotatable in relation to the housing cylinder. The mixing elements 12 at the front end of the mixing tube are located within the orifice of the mixing tube. Provided on the outer circumference of the mixing tube 11 is a sealing lip 14 which seals off, fluid-tight, the transition between the outer circumference of the mixing tube and the inner circumference of the housing cylinder 5. The sealing lip is designed flexibly in such a way that it slides along on the inner circumference of the housing cylinder 5 and offers only little frictional resistance during a displacement movement between the housing cylinder 5 and the mixing tube 11. The grip block 13 is of drum-like design and has grip faces 15 on two opposite sides. The diameter of the grip block 13 is larger than the diameter of the mixing tube 11 so that the grip block 13 forms a displacement abutment at the rear of the housing cylinder 5 or at the holding wings 7 when the mixing tube 11 is pushed into the housing cylinder 5. The mixing tube 11 runs completely through the grip block and is open at the rear end. Sliding passages 16 are provided on two mutually opposite sides, laterally next to the volume of the mixing tube, in the longitudinal direction in the grip block. The sliding passages 16 are arranged in the manner of a segment of a circle about the mixing tube 11 and extend from the front side to the rear side of the grip block. Insofar as the mixing tube 11 is introduced into the housing cylinder 5, the sliding passages 16 can come into alignment with the sliding channels in the strips 8 of the housing 1.

The discharge member 3 has a discharge tube 17 which runs in the longitudinal direction and which is closed off at the front end by a discharge face 18. The discharge tube 17 has arranged at its rear end a pressure plate 19 which extends transversally with respect to the discharge tube. On both sides of the discharge tube 17 extend sliding arms 20 which run parallel, project forward from the pressure plate 19 in a web-like manner and extend essentially as far as the front end of the discharge tube 17. A flexibly pretensionable latching arm 21 is arranged in each case at the front end of the sliding arms 20 on a longitudinal side of these. In the detentioned state, the latching arm 21 projects above the longitudinal face of the sliding arm 20 and can be pressed flexibly inward, so that it does not project above the face of the longitudinal side of the sliding arm 20. A latching boss 22 is arranged laterally on the outside of the latching arm 21.

The outside diameter of the discharge tube 17 is coordinated with an exact fit with the inside diameter of the mixing tube 11, so that the outer surface of the discharge tube 17 comes to lie on the inner surface of the mixing tube 11 and the discharge tube 17 is guided slideably inside the mixing tube 11. The transition between the outer circumference of the discharge tube 17 and the inner circumference of the mixing tube is sealed off, fluid-tight, by means of a sealing lip 23 at the front end of the discharge tube 17. When the discharge tube 17 is introduced into the mixing tube 11, the sliding arms 20 extend through the sliding passages 16 of the grip block 13 on the mixing tube 11 into the sliding channels in the strips 8 on the housing 1.

The housing cylinder 5, the mixing tube 11 and the discharge tube 17 are displaceable telescopically with respect to one another in the longitudinal direction. The discharge tube 17 is secured against twisting with respect to the housing cylinder 5, since the sliding arms 20 engage into the sliding channels of the strips 8 of the housing and therefore prevent the discharge member 3 from being twisted with respect to the housing 1. The mixing tube 11 arranged between the housing cylinder 5 and the discharge tube 17 is rotatable in relation to the housing cylinder 5 and to the discharge tube 17, since the sliding passages 16 extend circularly about the mixing tube 11 and have a greater length in the circumferential direction than the width of the sliding arms 20. The sliding arms 20 can therefore be moved within the sliding passages 16 in the circumferential direction about the mixing tube from one end of the sliding passage to the other end. The ends of the sliding passages 16 thus form an abutment for the rotational movement of the mixing tube 11 in relation to the discharge tube 17.

The cap 4 is of cylindrical design and on its outside has an external thread which can cooperate with the internal thread of the sleeve 9 on the housing 1. The cap 4 can thus be attached securely over the outlet 6 of the housing 1.

Figure 2A:
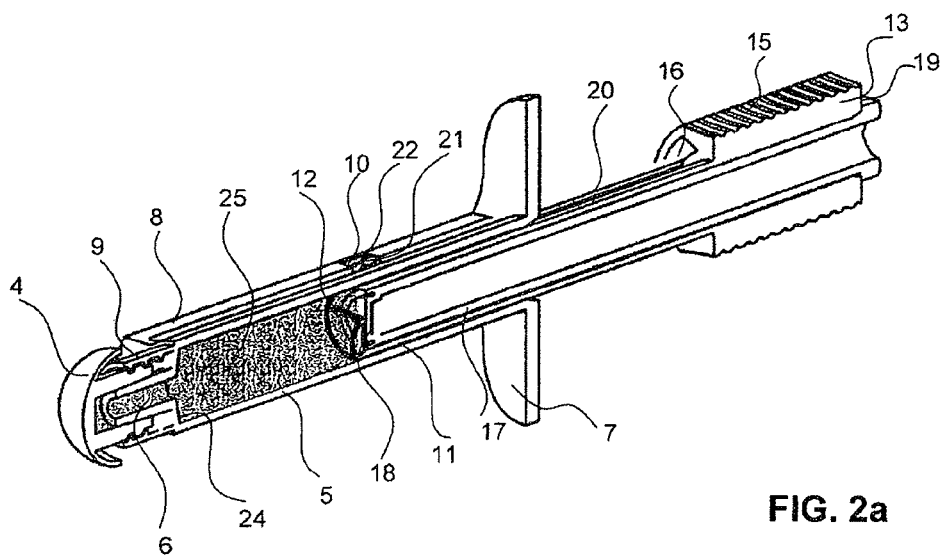
FIG. 2a: shows a longitudinal section through the first embodiment of a discharge apparatus according to the present invention in an initial position.

FIG. 2a shows the discharge apparatus according to FIG. 1 in the assembled state. The cover cap 4 is screwed into the sleeve 9 over the outlet 6. The discharge member 3 is pushed completely with the discharge tube 17 into the mixing tube 11 of the mixing device 2, so that the discharge face 18 abuts against the mixing elements 12. The rear face of the grip block 13 in this case butts against the pressure plate 19 at the rear end of the discharge tube 17. The discharge member 3 together with the mixing device 2 is partially inserted into the housing 1. For this purpose, the mixing tube 11, together with the discharge tube 17 located in it, is partially pushed into the housing cylinder 5. The sliding arms 20 in this case project into the sliding channels of the strips 8 on the housing 1 until the latching arms 21 engage into the latching orifices 10. In this case, the rear end of a latching arm 21 butts against the margin of the latching orifice 10, so that the sliding arm 20 cannot be drawn rearward out of the sliding channel. Withdrawal of the mixing tube 11 and of the discharge tube 17 out of the housing cylinder 5 is thereby blocked. Here, the latching boss 22 comes to lie in front of the opposite margin of the mixing tube. The latching boss 22 and the end of the latching arm 21, which both butt against the margin of the latching orifice 10, thus form a detention of the discharge member 3 inside the housing 1. Located inside the housing cylinder 5, between a cylinder bottom 24, in which the outlet 6 is located, and the discharge face 18 on the discharge tube 17, is a housing volume 25 in which a fluid product or even only one product component, such as, for example, a powder, is received.

Figure 2B:
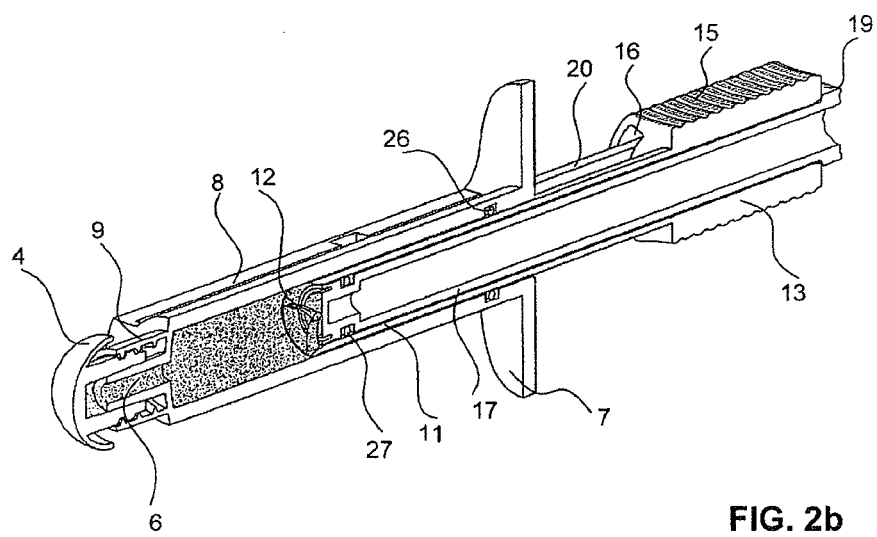
FIG. 2b: shows a longitudinal section through the discharge apparatus according to FIG. 2a with an alternative seal.

FIG. 2b shows a variant of the discharge apparatus according to FIG. 1, in which, instead of sealing lips for making a fluid-tight transition between the housing 1 and mixing tube 11 and between the mixing tube 11 and discharge tube 17, O-rings are used, for example produced from rubber. A first O-ring 26 is provided between the housing 1 and mixing tube 11 in a circumferential groove in the inner wall of the housing and bears against the outer wall of the mixing tube 11. A second O-ring 27 is arranged between the mixing tube 11 and discharge tube 17 in a circumferential groove in the outer circumference of the discharge tube 17 and bears against the inner wall of the mixing tube 11. The O-rings 26 and 27 close off, fluid-tight, the housing volume 25, but allow a simple displacement of the mixing tube 11 and discharge tube 17 in relation to the housing 1.

The state of the discharge apparatus according to FIGS. 2a and 2b corresponds, for example, to a storage or delivery state before the discharge apparatus is used.

Figure 3:
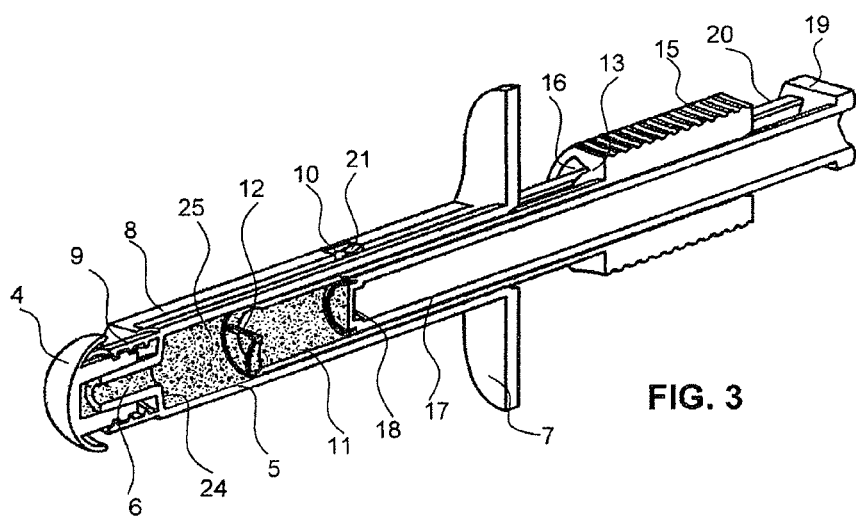
FIG. 3: shows a longitudinal section of the discharge apparatus during a mixing operation.

FIG. 3 shows the discharge apparatus during an operation to mix the fluid product. To mix the fluid product in the housing volume 25, the mixing tube 11 is gripped with one hand at the grip face 15 on the grip block 13, and, for example, the housing 1 is held with the other hand. The mixing tube 11 is moved forward and backward by means of the grip block 13 between the front abutment at the holding wings 7 of the housing and the rear abutment on the pressure plate 19 of the discharge member. In this case, the mixing tube 11 is displaced within the housing cylinder 5 between the housing cylinder 5 and the discharge tube 17. The discharge tube 17 remains fixed in relation to the housing cylinder, since the latching arm 21 of the sliding arm 20 engages into the latching orifice 10 within the sliding channel of the strips 8. During the displacement of the mixing tube 11, the mixing elements 12 are moved to and fro between the bottom 24 of the housing cylinder 5 and the discharge face 18 of the discharge tube 17. The mixing elements 12 cause swirling of the fluid product within the housing volume 25. When the mixing tube 11 is pushed forward, the fluid product is in this case received inside the mixing tube 11 and, when the mixing tube 11 is pushed back, is expelled from the mixing tube again by means of the discharge face 18.

It is possible that residues or particles of the fluid product remain adhering to the bottom 24 and to the discharge face 18. In order to release these, the mixing tube can be rotated inside the housing cylinder 5. For this purpose, the mixing tube, in the foremost position in which the mixing elements 12 bear against the bottom 24 of the housing cylinder 5, is rotated by means of the grip block 13 about the discharge tube 17 within the sliding passages 16. During this rotation, the mixing elements 12 scrape over the surface of the bottom 24 and can release adhering fragments of the fluid product. In the rear-most position of the mixing tube 11, in which the grip block 13 butts against the pressure plate 19, the mixing elements 12 bear against the discharge face 18 of the discharge tube 17. In this position, once again, the mixing tube 11 is rotated about the discharge tube 17 by means of the grip block 13, so that the mixing elements 12 scrape over the discharge face 18 and release adhering material of the fluid product.

Figure 4:
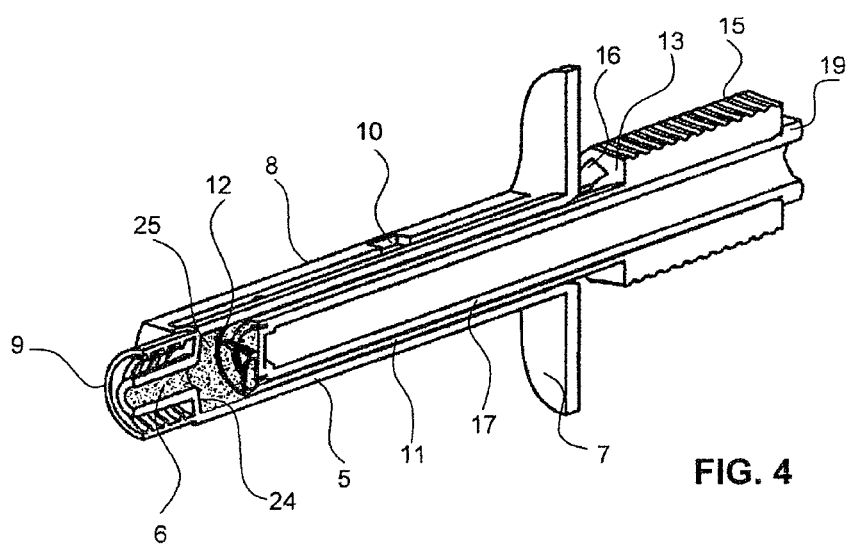
FIG. 4: shows a longitudinal section of the discharge apparatus during the discharge of a fluid.

After the mixing operation has ended, the fluid product can be discharged from the discharge apparatus. As shown in FIG. 4, to discharge the product the cap 4 is removed from the outlet 6. The discharge tube 17 is pushed into the housing cylinder 5 in the direction of advance in relation to the housing cylinder 5. For this purpose, for example, the housing 1 is held between the index finger and middle finger, so that the holding wings 7 bear against the fingers and the thumb engages on the pressure plate 19. When the fingers are pressed together in order to push the discharge tube 17 into the housing cylinder 5, an initial resistance first has to be overcome which is generated by the butting of the latching boss 22 against the margin of the latching orifice 10. By pressure upon the discharge tube 17 in the longitudinal direction, force is generated by the margin of the latching orifice 10 upon the latching arm 21 and seeks to bend the latter inward. As soon as the initial resistance of the latching boss 22 is overcome, the latching arm 21 sinks within the housing cylinder 5, so that less force is required in order to push the discharge tube 17 further forward. During the advance of the discharge tube 17, the discharge face 18 presses against the fluid product within the housing volume 25 and expels it out of the housing cylinder 5 through the outlet 6.

Figure 5:
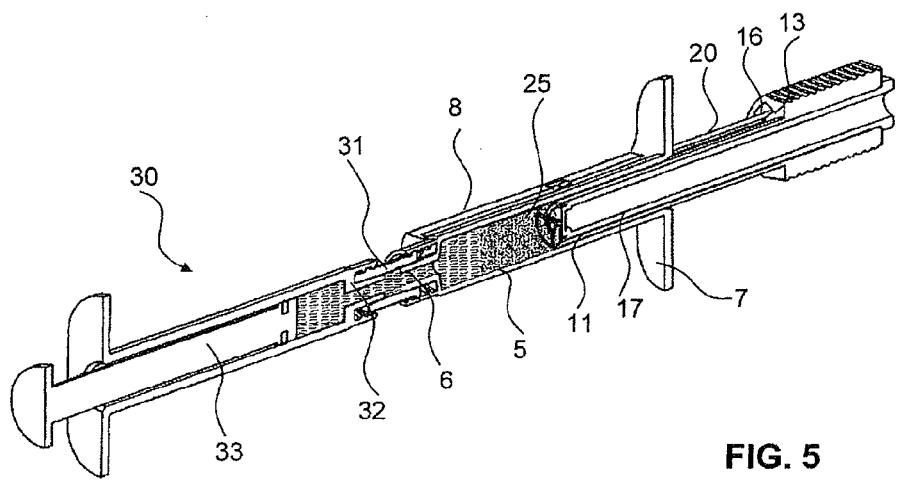
FIG. 5: shows a longitudinal section through a discharge apparatus with a loading apparatus.

FIG. 5 shows a system composed of a discharge apparatus according to the invention and of a loading apparatus 30 in the form of a syringe. The syringe is coupled to the outlet 6 of the discharge apparatus by means of a coupling piece 31. A fluid connection in this case occurs between the outlet 6 and an outlet 32 of the syringe 30. The content of the syringe 30 can then be administered into the housing volume 25 of the housing cylinder 5 through the outlet 32 and the outlet 6 by means of an advance member 33. In this case, the discharge member 3 is pressed out of the housing 1 since the product introduced presses against the discharge face 18.

In the example shown, one component of the fluid product is already stored inside the housing volume 25 of the housing 1. This component may, for example, be a powder. A second component is introduced into the discharge apparatus from the syringe 30, in order, together with the first component, to form the desired fluid product. As soon as the second component has been transferred completely out of the loading apparatus 30 into the discharge apparatus, the coupling piece 31 can be removed from the outlet 6. The cap 4 is then attached over the outlet 6, and a mixing operation, as described with regard to FIG. 3, can be carried out within the discharge apparatus by means of the mixing device.

Figure 6:
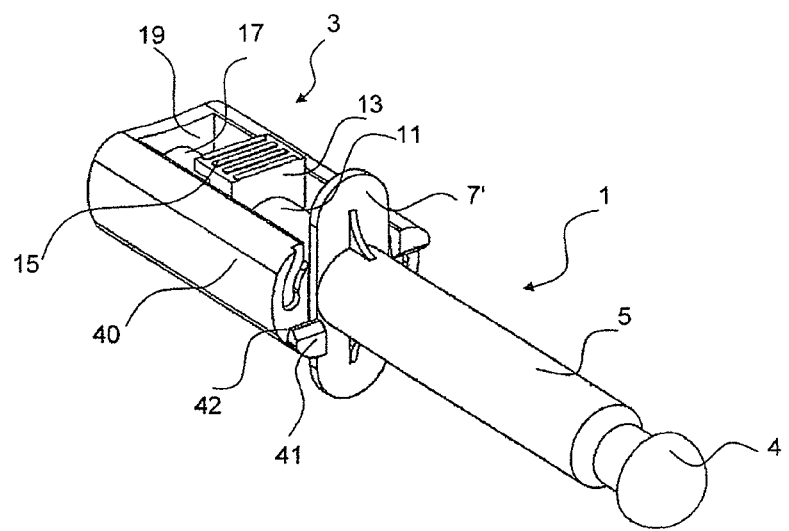
FIG. 6: shows a three-dimensional illustration of a second embodiment of a discharge apparatus according to the present invention in an unlocked position.

FIG. 6 shows a second embodiment of a discharge apparatus according to the present invention. Structural parts comparable to those of the first embodiment are designated by the same reference symbols. The discharge apparatus comprises a housing 1 with a housing cylinder 5, a mixing device with a mixing tube 11, and a discharge member 3 with a discharge tube 17. A cover cap 4 is arranged at the front end of the housing cylinder 5. Two holding or latching wings 7' are arranged so as to project radially at the rear end. The mixing tube 11 comes to lie inside the housing cylinder 5 and the discharge tube 17 is guided inside the mixing tube 11. Provided at the rear end of the discharge tube 17 is a pressure plate 19, from which two outriggers 40 project parallel to the discharge tube 17 on both sides of said discharge tube. The outriggers 40 thus flank the discharge tube 17 on both sides. At the rear end of the mixing tube 11, a grip block 13 is provided, which comes to lie between the two outriggers 40. The side faces of the mixing tube 11 in this case come to lie on the inner faces of the outriggers 40 and can slide along these.

The outriggers 40 thus form a guide for the grip block 13 when the mixing tube 11 is displaced in relation to the discharge member inside the housing cylinder 5. Furthermore, the grip block 13 has grip faces 15 which project slightly above the lateral faces of the outriggers 40.

To displace the discharge member 3 within the housing cylinder 5, the housing cylinder 5 is brought into a rotary position in which the latching wings 7' come to lie between the outriggers 40. In this position, the discharge tube 17 can be pushed into the housing cylinder 5, the two outriggers 40 sliding past the two opposite sides of the housing cylinder 5 and receiving between themselves the latching wings 7'. The outriggers 40 thus form a guide device for the discharge member 3 during the advance of the discharge tube 17 in the housing 1.

At the front end of the outriggers 40, latching hooks 41 projecting in the longitudinal direction of the outriggers are arranged on the front face. The latching hooks 41 are designed in such a way that they form a latching groove 42 between the front face of the outriggers 40 and the hook. The orifice of such a latching groove is oriented in the circumferential direction of the housing cylinder. A latching hook 41 is provided on each of the two opposite outriggers 40 point-symmetrically to the longitudinal axis of the housing cylinder. The orifices of the latching grooves therefore point circumferentially in the same direction.

Figure 7:
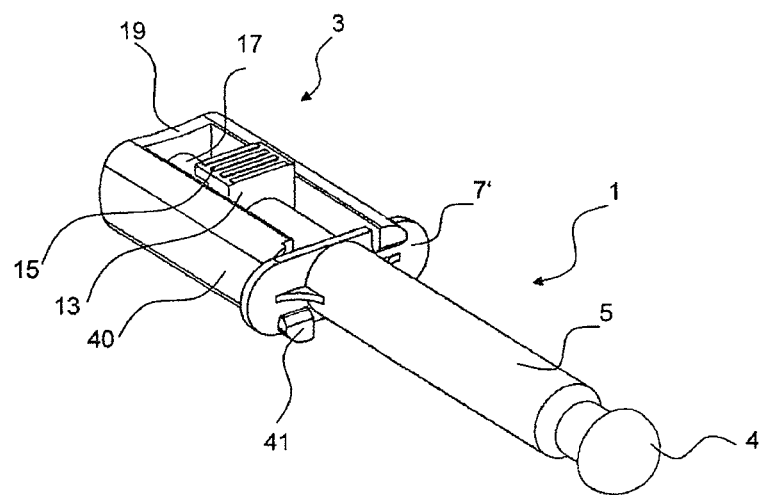
FIG. 7: shows the discharge apparatus according to FIG. 6 in a locked position.

FIG. 7 shows the discharge apparatus in a detained position in which the discharge member 3 is detained in relation to the housing 1. For this purpose, the discharge member 3 has been drawn out of the housing cylinder 5 until the front side of the outriggers 40 comes to lie behind the latching wings 7'. The discharge member 3 is then rotated in relation to the housing 1 in such a way that the latching wings 7' slide past the front sides of the outriggers 40 until said latching wings engage into the latching grooves 42 on the latching hooks 41. In this detaining position, the discharge member 3 is detained with respect to longitudinal movement in relation to the housing 1.

To mix a fluid product inside the housing cylinder 5, the mixing tube 11 can then be moved forward and backward in the housing cylinder 5 by means of the grip block 13. For this purpose, the grip block 13 is pushed to and fro between the outriggers 40 from a rear abutment on the pressure plate 19 to a front abutment on the latching wings 7'. After the mixing operation has ended, the discharge member 3 can be rotated in the opposite direction in relation to the housing 1, so that the latching wings 7' are rotated out of the latching hooks. The latching hooks preferably project from the front side of the outriggers 40 to extend such that, in this direction of rotation, said latching hooks form an abutment for the latching wings 7'. As soon as the latching wings 7' butt against the latching hooks, the latching wings 7' come to lie between the outriggers 40, and the discharge tube 17 can be pushed into the housing cylinder 5 by pressure upon the pressure plate 19. After the cap 4 has been removed, the mixed fluid product can thereby be discharged through the outlet on the housing cylinder 5.

LIST OF REFERENCE SYMBOLS

1 Housing
2 Mixing device
3 Discharge member
4 Cover cap
5 Housing cylinder
6 Outlet
7 Holding wing
7' Latching wing 8 Strips, sliding channel
9 Sleeve
10 Latching orifice
11 Mixing tube
12 Mixing element
13 Grip block
14 Sealing lip
15 Grip face
16 Sliding passage
17 Discharge tube
18 Discharge face
19 Pressure plate
20 Sliding arm
21 Latching arm
22 Latching boss
23 Sealing lip
24 Bottom
25 Housing volume
30 Loading apparatus
31 Coupling piece
32 Outlet
33 Advance member
40 Outrigger
41 Latching hook
42 Latching groove

The invention claimed is:

1. A discharge apparatus for discharging a fluid product, comprising:
   a housing with an outlet at a front housing end,
   a discharge member which is mounted moveably in the housing and projects with its rear end out of a rear housing end,
   a mixing device for mixing the fluid product inside the housing, the mixing device having a mixing tube, which has a front end, and which is mounted moveably in the housing between the housing and the discharge member, and having at least one mixing element, which is arranged at the front end of the mixing tube,
   a housing volume being formed between the outlet and the discharge member, the mixing element being arranged inside the housing volume, the fluid product being provided in the housing volume and being dischargeable out of the housing through the outlet as a result of the advance of the discharge member inside the housing from a rear position into a front position in the direction of the outlet,
   wherein at least one sliding arm is provided on the discharge member, and at least one sliding channel, in which the sliding arm is mounted slideably, is provided on the housing,
   and wherein at least one latching element is provided on the at least one sliding arm and releasably latches together with at least one counter latching element which is provided in the sliding channel, in order to achieve a releasable detention of the discharge member in the rear position.

2. The discharge apparatus as claimed in claim 1, wherein the mixing tube projects with its rear end out of the rear housing end.

3. The discharge apparatus as claimed in claim 1, wherein the discharge member is arranged at least partially within the mixing tube.

4. The discharge apparatus as claimed in claim 1, wherein the discharge member projects out of the rear end of the mixing tube.

5. The discharge apparatus as claimed claim 1, wherein the mixing tube has, at the rear end projecting out of the housing, a grip block which is arranged between the rear housing end and the rear end of the discharge member.

6. The discharge apparatus as claimed in claim 5, wherein the housing has a housing abutment at the rear end and the discharge member has a stop abutment at the rear end, between which abutments the grip block of the mixing tube is displaceable.

7. The discharge apparatus as claimed in claim 1, wherein an outer wall of the mixing tube is mounted, fluid-tight, on an inner wall of the housing, and the discharge member is mounted, fluid-tight, on the inner wall of the mixing tube.

8. The discharge apparatus as claimed in claim 1, wherein the mixing tube is mounted rotatably in relation to the housing and/or the discharge member.

9. The discharge apparatus as claimed in claim 1, wherein, in a rear position of the discharge member in relation to the housing, the mixing tube is moveable between a front and a rear position within the housing volume for the purpose of mixing the fluid product, the fluid product being received within the mixing tube in the front position.

10. The discharge apparatus as claimed in claim 1, wherein the at least one latching element is formed by at least one latching arm projecting flexibly from the sliding arm and the at least one counter latching element is formed by at least one latching orifice in a sliding face of the sliding channel, the latching arm engaging into the latching orifice in the rear position of the discharge member in relation to the housing.

11. The discharge apparatus as claimed in claim 1, wherein a detaining device is formed by at least one latching wing on one of the housing and discharge member, and at least one latching groove is formed on the other of the housing and discharge member, the at least one latching wing being introduced releasably into the at least one latching groove as a result of a rotational movement between the housing and discharge member in the rear position of the discharge member.

12. The discharge apparatus as claimed in claim 1, wherein a blocking device for blocking movement of the discharge member in the rear position in relation to the housing opposite to a direction of advance is provided.

13. The discharge apparatus as claimed in claim 12, wherein the blocking device is formed by one end of a latching arm and a margin of a latching orifice as an abutment for the latching arm end.

14. The discharge apparatus as claimed in claim 1, wherein a guide device for guiding a grip block of the mixing tube during displacement along the discharge member is provided.

15. The discharge apparatus as claimed in claim 14, wherein the guide device is formed by at least one sliding arm or outrigger which runs parallel to the discharge member and which is arranged on the discharge member.

16. A system composed of a loading apparatus and of a discharge apparatus for discharging a fluid product, the discharge apparatus comprising:
   a housing with an outlet at a front housing end,
   a discharge member which is mounted moveably in the housing and projects with its rear end out of a rear housing end,
   a mixing device for mixing the fluid product inside the housing, the mixing device having a mixing tube, which has a front end, and which is mounted moveably in the housing between the housing and the discharge member, and having at least one mixing element, which is arranged at the front end of the mixing tube,
   a housing volume being formed between the outlet and the discharge member, the mixing element being arranged inside the housing volume, the fluid product being provided in the housing volume and being dischargeable out of the housing through the outlet as a result of the advance of the discharge member inside the housing from a rear position into a front position in the direction of the outlet, wherein at least one sliding arm is provided on the discharge member, and at least one sliding channel, in which the sliding arm is mounted slideably, is provided on the housing, and wherein at least one latching element is provided on the at least one sliding arm and releasably latches together with at least one counter latching element which is provided in the sliding channel, in order to achieve a releasable detention of the discharge member in the rear position, a first mix component being accommodated in the housing volume of the discharge apparatus, and a second mix component being introducible into the housing volume from the loading apparatus.

* * * * *